(12) United States Patent
Krimsky

(10) Patent No.: US 10,952,799 B2
(45) Date of Patent: Mar. 23, 2021

(54) SYSTEMS AND METHODS FOR NAVIGATIONAL BRONCHOSCOPY AND SELECTIVE DRUG DELIVERY

(71) Applicant: COVIDIEN LP, Mansfield, MA (US)

(72) Inventor: William S. Krimsky, Forest Hill, MD (US)

(73) Assignee: COVIDIEN LP, Mansfield, MA (US)

( * ) Notice: Subject to any disclaimer, the term of this patent is extended or adjusted under 35 U.S.C. 154(b) by 301 days.

(21) Appl. No.: 15/921,966

(22) Filed: Mar. 15, 2018

(65) Prior Publication Data

US 2018/0344410 A1 Dec. 6, 2018

Related U.S. Application Data

(60) Provisional application No. 62/512,764, filed on May 31, 2017.

(51) Int. Cl.
*A61B 5/00* (2006.01)
*A61B 34/20* (2016.01)
(Continued)

(52) U.S. Cl.
CPC .......... *A61B 34/20* (2016.02); *A61B 1/00087* (2013.01); *A61B 1/2676* (2013.01); *A61B 5/062* (2013.01); *A61B 34/10* (2016.02); *A61B 90/361* (2016.02); *A61B 90/37* (2016.02); *A61M 16/0463* (2013.01); *A61B 2017/00809* (2013.01); *A61B 2034/105* (2016.02); *A61B 2034/107* (2016.02); *A61B 2034/2051* (2016.02); *A61B 2034/252* (2016.02); *A61B 2090/373* (2016.02); *A61B 2090/374* (2016.02); *A61B 2090/378* (2016.02); *A61B 2090/3762* (2016.02); *A61B 2090/3941* (2016.02);
(Continued)

(58) Field of Classification Search
None
See application file for complete search history.

(56) References Cited

U.S. PATENT DOCUMENTS 6,188,355 B1 2/2001 Gilboa
7,233,820 B2 6/2007 Gilboa
(Continued)

FOREIGN PATENT DOCUMENTS

EP 2508221 A1 10/2012
WO 0010456 A1 3/2000
(Continued)

OTHER PUBLICATIONS

Extended European Search Report issued in Appl. No. EP 18175032.4 dated Oct. 30, 2018 (7 pages).
(Continued)

*Primary Examiner* — Joel F Brutus

(57) ABSTRACT

Provided in accordance with the present disclosure is a diagnostic and a therapeutic bronchoscopy system for localized delivery of medication within the lungs. Specifically, systems and methods are disclosed for creating a functional and anatomical map of the lungs, diagnosing a condition within the lungs, generating a treatment plan for a target site within the lungs, navigating to the target site, administering a treatment directly to the target site for immediate absorption within the target site, and assessing the efficacy of the treatment.

21 Claims, 3 Drawing Sheets

(51) Int. Cl.
  *A61B 1/267* (2006.01)
  *A61M 16/04* (2006.01)
  *A61B 5/06* (2006.01)
  *A61B 90/00* (2016.01)
  *A61B 1/00* (2006.01)
  *A61B 34/10* (2016.01)
  *A61B 17/00* (2006.01)
  *A61B 34/00* (2016.01)
  *A61M 11/02* (2006.01)

(52) U.S. Cl.
  CPC ..... *A61M 11/02* (2013.01); *A61M 2205/3317* (2013.01); *A61M 2205/502* (2013.01); *A61M 2205/581* (2013.01); *A61M 2205/584* (2013.01)

(56) References Cited

U.S. PATENT DOCUMENTS

| | | |
|---|---|---|
| 9,247,992 B2 | 2/2016 | Ladtkow et al. |
| 2002/0086852 A1* | 7/2002 | Cantor ................. A61K 9/0078 514/54 |
| 2003/0051733 A1 | 3/2003 | Kotmel et al. |
| 2004/0011364 A1* | 1/2004 | Dhuper ............. A61M 16/0484 128/207.14 |
| 2011/0245665 A1 | 10/2011 | Nentwick |
| 2014/0018616 A1 | 1/2014 | Melsheimer et al. |
| 2015/0272666 A1 | 10/2015 | Wang |
| 2016/0000520 A1 | 1/2016 | Lachmanovich et al. |
| 2016/0051221 A1* | 2/2016 | Dickhans ............... A61B 8/085 600/424 |
| 2016/0183888 A1 | 6/2016 | Averbuch |
| 2016/0188806 A1 | 6/2016 | Stopek |
| 2016/0263187 A1* | 9/2016 | Lander ................. A61K 31/555 |
| 2016/0317233 A1 | 11/2016 | Hunter et al. |
| 2017/0035380 A1 | 2/2017 | Barak et al. |
| 2017/0065523 A1* | 3/2017 | Nguyen ............. A61K 31/7068 |

FOREIGN PATENT DOCUMENTS

| | | |
|---|---|---|
| WO | 0167035 A1 | 9/2001 |
| WO | 2004101028 A2 | 11/2004 |
| WO | 2012158500 A1 | 11/2012 |
| WO | 2014124241 A1 | 8/2014 |

OTHER PUBLICATIONS

Office Action issued in corresponding Chinese Appl. No. 201810543234.9 dated Jun. 2, 2020 (9 pages) together with English language translation (8 pages).

* cited by examiner

SYSTEMS AND METHODS FOR NAVIGATIONAL BRONCHOSCOPY AND SELECTIVE DRUG DELIVERY

CROSS REFERENCE TO RELATED APPLICATION

The present application claims the benefit of and priority to U.S. Provisional Application Ser. No. 62/512,764, filed on May 31, 2017 the entire contents of which are incorporated herein by reference.

BACKGROUND

1. Technical Field

The present disclosure relates to surgical systems, and more particularly, to systems and methods for diagnosis, navigation, and localized treatment of lung conditions.

2. Discussion of Related Art

Tens of millions of people suffer from lung disease, such as emphysema, chronic obstructive pulmonary disease ("COPD"), asthma, interstitial lung disease, cystic fibrosis, cancer, pulmonary edema, or myriad other afflictions affecting the lungs.

As can be appreciated, trapped volumes of air, swelling, mucus, or other fluids in the lungs caused by lung disease make it difficult to effectively deliver inhaled medications to target sites deep within the lungs (e.g., bronchus, bronchioles, alveoli), which are often most in need of the medication, but are the least likely to receive it. Moreover, it is often difficult to immediately determine the efficacy of a particular medication after it has been administered to the patient. Therefore, a need exists for a diagnostic and a therapeutic bronchoscopy system for localized delivery of therapies and diagnostic agents within the lungs for treatment of lung disease.

SUMMARY

Provided in accordance with aspects of the present disclosure is a method for generating a three-dimensional (3D) model of a luminal network from a plurality of images and generating a navigational plan based on the 3D model to navigate to a target site within the luminal network. The method may include navigating, using the 3D model, a flexible elongate member including a therapeutic and diagnostic agent dispenser coupled thereto to the target site. The therapeutic and diagnostic agent dispenser may be configured to dispense aerosolized particles to treat the target site. The method may include administering the aerosolized particles from the therapeutic and diagnostic agent dispenser directly to the target site for absorption within the target site.

In an aspect of the present disclosure, the aerosolized particles are selected from the group consisting of liquids, gases, and gels.

In another aspect of the present disclosure, the method includes performing a scan selected from the group consisting of ventilation-perfusion (VQ), functional respiratory imaging, MRI, ultrasound, and computer tomography during a respiratory cycle to further refine the 3D model of the luminal network.

In yet another aspect of the present disclosure, administering the aerosolized particles includes delivering a time release therapeutic agent.

In still another aspect of the present disclosure, the method includes assessing the efficacy of the aerosolized particles using the 3D model of the luminal network.

In another aspect of the present disclosure, assessing the efficacy of the aerosolized particles includes comparing a pre-treatment 3D model of the luminal network with a post-treatment 3D model of the luminal network to determine a response to the aerosolized particles.

In yet another aspect of the present disclosure, the method includes selecting a therapeutic or diagnostic agent to deliver to the target site.

In still another aspect of the present disclosure, the method includes selecting a specific airway within a patient's lungs.

In still yet another aspect of the present disclosure, the method includes providing a bronchoscope having the therapeutic or diagnostic agent dispenser at a distal end thereof and inserting the bronchoscope and the therapeutic and diagnostic agent dispenser through a patient's nose and administering the aerosolized particles in an outpatient setting.

Provided in accordance with another aspect of the present disclosure is a system a display presenting one or images of a patient's lungs, a user interface presented on the display configured to present a three-dimensional (3D) model of a luminal network, wherein the 3D model is configured to assist a clinician in navigating to a target site within the luminal network. The system may further include a working channel navigable within the luminal network and a flexible elongate member and a therapeutic and diagnostic agent dispenser coupled thereto configured to dispense aerosolized particles to treat the target site, the flexible elongate member and the therapeutic and diagnostic agent dispenser configured for advancement through the working channel to deliver the aerosolized particles directly to the target site for absorption within the target site.

In an aspect of the present disclosure, the aerosolized particles are selected from the group consisting of liquids, gases, and gels.

In another aspect of the present disclosure, the therapeutic and diagnostic agent dispenser is an aerosol emitting device for deploying the aerosolized particles onto the target site.

In yet another aspect of the present disclosure, the therapeutic and diagnostic agent dispenser is an atomizer.

In still another aspect of the present disclosure, the therapeutic and diagnostic agent dispenser is a nebulizer.

In still yet another aspect of the present disclosure, each particle of the aerosolized particles is between 5 and 15 microns in diameter upon dispensation.

In another aspect of the present disclosure, the 3D model of the luminal network is formed from a computed tomography (CT) scan, the 3D model configured to be merged together with images from a second imaging modality to facilitate navigation through the lung's airways and to treat tissue.

In yet another aspect of the present disclosure, the user interface is configured to assess an efficacy of the aerosolized particles.

In still another aspect of the present disclosure, the user interface is configured to compare a pre-treatment 3D model of the luminal network with a post-treatment 3D model of the luminal network such that an efficacy of the aerosolized particles can be determined.

In still yet another aspect of the present disclosure, a therapeutic agent is selected from the group consisting of bronchidilators, corticosteroids, methylxanthines, beta-agonists, inhibitors, antimicrobials, antitumor agents, antifibrotic agents, biologic agents, immunotherapy, gene vectors, radio-labeled and auto fluorescing ligands.

In another aspect of the present disclosure, a diagnostic agent is selected from the group consisting of inorganic and organic compounds, dyes, stains, radioactive tracers, and culture-media chemical based constituents.

BRIEF DESCRIPTION OF THE DRAWINGS

Objects and features of the presently disclosed system and method will become apparent to those of ordinary skill in the art when descriptions of various embodiments thereof are read with reference to the accompanying drawings, wherein.

DETAILED DESCRIPTION

Provided in accordance with the present disclosure is a diagnostic and a therapeutic bronchoscopy system for localized delivery of therapies and diagnostic agents, medications, etc. within the lungs. One of the challenges of respiratory medicine is the delivery of inhaled agents or medications to precise locations to best identify or treat a variety of different lung diseases such as obstructive lung diseases, given the dynamic nature of respiration in the context of relatively limited system measures such as forced vital capacity (FVC) and the like. The primary mode of delivery remains through the oropharynx (i.e., the throat). For many reasons (e.g., swelling, mucus, trapped air, anatomy), the inhaled medications do not or cannot make it to the lower respiratory airways and thus, cannot provide effective treatment to the areas of the lungs that need it most. The described system provides a clinician with the ability to distribute a therapeutic or diagnostic agent or medication directly to a target site for ensured delivery and the ability to assess the efficacy of that agent or medication during both static as well as dynamic assessments and/or after a procedure. Specifically, the present disclosure discloses systems and methods for creating and fusing functional and anatomical maps of the lungs, diagnosing a condition within the lungs, generating a treatment plan for a target site within the airways or lungs, navigating to a target site, administering a therapeutic or diagnostic agent or treatment to the target site, and assessing the efficacy of the agent or treatment. These and other aspects and features of the present disclosure are detailed herein below.

Figure 1:
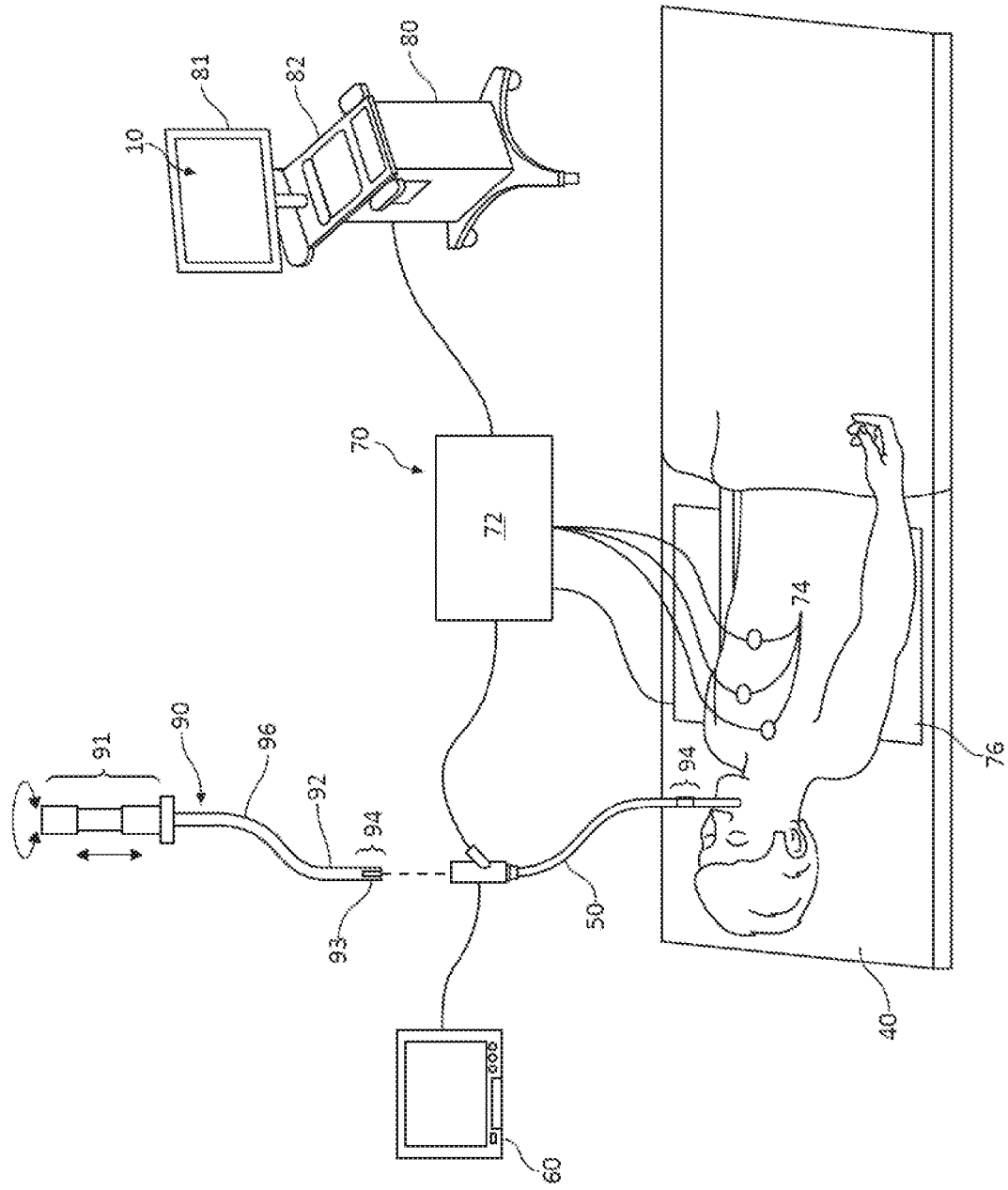
FIG. 1 is a perspective schematical view of an electromagnetic navigation system in accordance with the present disclosure.

Referring initially to FIG. 1, an illustration of an electromagnetic navigation (EMN) system 10 in accordance with the present disclosure is shown. The EMN system 10 may be used for planning and navigating a pathway to a target tissue site and delivering a therapeutic or diagnostic agent or dose of medication to the target site, as will be described in further detail below. EMN system 10 generally includes an operating table 40 configured to support a patient, a bronchoscope 50 configured for insertion through the patient's mouth and/or nose into the patient's airways, monitoring equipment 60 coupled to bronchoscope 50 for displaying video images received from bronchoscope 50, a tracking system 70 including a tracking module 72, a plurality of reference sensors 74, an electromagnetic field generator 76, and a workstation 80 including software and/or hardware used to facilitate pathway planning, identification of target tissue, and navigation to target tissue. EMN system 10 also includes a catheter assembly 90, which is insertable into the working channel of bronchoscope 50. As will be described in further detail below, catheter assembly 90 and other treatment tools may be inserted through bronchoscope 50 to navigate to and/or treat tissue.

As part of the planning phase, a series of pre-procedure images of the patient airways are obtained using one or more imaging modalities, such as computerized tomography (CT) scans, and used for planning and generating the pathway to the target. Generally, during imaging, the patient's breath is held during the CT scan thereby creating a single set of image slices (e.g., CT image data) based on either the peak inhalation or peak exhalation of a patient's respiratory cycle. The CT image data is then loaded onto workstation 80, which utilizes the CT image data for generating and viewing a three-dimensional map or model of the patient's airways. The 3D model and image data derived from the 3D model enables the identification of the target tissue (automatically, semi-automatically or manually), and allows for the selection of a pathway through the patient's airways to the target tissue, which in fact may be the airways themselves. More specifically, the CT scans are processed and assembled into a 3D volume, which is then utilized to generate the 3D model of the patient's airways. Additionally, a more dynamic anatomic map of the airways can also be rendered in 3D using CT or other modalities in order to make an assessment of the airway tree and lung during normal tidal volume breathing such that targets, targeted treatment areas, etc., can be better identified.

The 3D model may be presented on a display monitor 81 associated with workstation 80, or in any other suitable fashion. Using workstation 80, various slices of the 3D volume and views of the 3D model may be presented and/or may be manipulated by a clinician to facilitate identification of the target tissue and selection of a suitable pathway through the patient's airways to access the target tissue. The 3D model may also show marks of the locations where previous biopsies were performed, including the dates, times, and other identifying information regarding the tissue samples obtained. These marks may also be selected as the target site to which a pathway can be planned. Once selected, the pathway is saved for use during the navigation procedure. The 3D model and real time images of the lungs are then merged together (similar to car GPS), to facilitate navigation through the lung's airways and to treat tissue. The 3D model can be updated based on dynamic feedback from, e.g., the treatment affect on the airways or lack thereof, the need for further treatment, additional diagnoses, under treated or over treated areas, or simply as a consequence of the merged image data determining where to direct the treatment for optimal clinical effect. The information generated from the 3D model described above can be used to develop a database such that 3D model, maps, and other patient data, may be optimized over time relative to the disease or affliction being targeted.

It should be appreciated that a patient's lungs may additionally or alternatively be imaged using any suitable imaging device, such as MRI, ultrasound, PET, and/or the like, and the images may be processed in combination with the software and programs stored on workstation 80, described in greater detail below.

One example of an EMN system that generates 3-D models of airways and other luminal networks from CT image data is the ILOGIC® ELECTROMAGNETIC NAVIGATION BRONCHOSCOPY® system, currently sold by Covidien LP. The details of such a system are described in the commonly assigned U.S. Pat. No. 7,233,820 filed on Mar. 29, 2004 to Gilboa and entitled ENDOSCOPE STRUCTURES AND TECHNIQUES FOR NAVIGATING TO A TARGET IN BRANCHED STRUCTURE, the contents of which are incorporated herein by reference.

During the planning phase, scan traceable particles may be administered to a patient to assess where the scan traceable particles ultimately disperse to in the lungs (e.g., the deposition pattern) and where the most functional lung and gas exchange occurs. Such an assessment may be performed, for example, by using functional respiratory imaging, ventilation-perfusion (VQ) scan, CT, MRI, ultrasound, PET, or a combination thereof, which can also create both dynamic and static maps. The dynamic and static maps may be overlaid and/or integrated with previous patient imaging (e.g., models, maps, etc.) to refine the 3D model. Inhaled medications, e.g., bronchodilators, antibiotics, etc., can then be used to evaluate potential alternations or changes from the previous patient models or maps, which can then be integrated into the treatment plan to refine the treatment plan therewith (e.g., identify over treated or under treated areas and treating such areas). In at least one embodiment, comparison of localized lung function and structural changes (e.g., diameter of airways) before and after administration can be utilized to assess where in the lungs the bronchodilator, tracer and/or other therapy reaches and locations requiring specialized treatment. When the bronchodilator, tracer and/or other therapy is administered in combination with scan traceable particles, the aerosolized deposition pattern at various points in the respiratory cycle may then be visible under imaging such as MRI, functional respiratory imaging, PET, V/Q scanning and the like. This imaging information may be used to further refine the 3-D imaging map of the patient's lungs or to determine which areas of the lungs are not receiving and/or are incapable of receiving medication (e.g., due to swelling, air or mucus build up, or other condition), and to identify locations for localized treatment using the procedures and devices described herein.

Referring still to FIG. 1, catheter guide assembly 90 usable with EMN system 10 is shown. Catheter guide assembly 90 includes a handle 91, which is connected to an extended working channel (EWC) 96. The EWC 96 is sized for placement into the working channel of bronchoscope 50 and allows for deep access into the lung. In operation, a locatable guide (LG) 92, including an electromagnetic (EM) sensor 94, is inserted into the EWC 96 and locked into position such that the sensor 94 extends a desired distance beyond the distal tip of the EWC 96. In one embodiment, the LG 92 is integrated with the EWC 96 so the EM sensor 94 is disposed on the EWC 96. The location of the EM sensor 94, and thus the distal end of the EWC 96, within an electromagnetic field generated by the electromagnetic field generator 76, can be derived by the tracking module 72 and the workstation 80. Catheter guide assembly 90 further includes a handle 91 that can be manipulated by rotation and compression to steer a distal tip 93 of the LG 92 and extended working channel (EWC) 96. Catheter guide assembly 90 is currently marketed and sold by Medtronic, Inc. under the names SUPERDIMENSION® and EDGE™ Procedure Kits. For a more detailed description of catheter guide assembly 90, reference may be made to commonly-owned U.S. Pat. No. 9,247,992 filed on Mar. 15, 2013 by Ladtkow et al., the entire contents of which are hereby incorporated by reference.

As illustrated in FIG. 1, the patient is shown lying on an operating table 40 with a bronchoscope 50 inserted through the patient's mouth and into the patient's airways. Bronchoscope 50 may include a source of illumination (not explicitly shown) and a video imaging system (not explicitly shown) and is coupled to monitoring equipment 60, e.g., a video display, for displaying the video images received from the video imaging system of bronchoscope 50.

Catheter guide assembly 90, including LG 92 and EWC 96, is configured for insertion through a working channel of bronchoscope 50 into the patient's airways (although the catheter guide assembly 90 may alternatively be used without bronchoscope 50). EM sensor 94 may be disposed directly on the EWC 96, as described above. Additionally, or alternatively, EM sensor 94 may be disposed directly on or built into bronchoscope 50, or fitted over the bronchoscope 50 in the form of an adapter (not shown). The sensor 94 may be disposed anywhere along the channel of the bronchoscope 50. A six degrees-of-freedom (DOF) electromagnetic tracking system 70 may be used and may be similar to those disclosed in U.S. Pat. No. 6,188,355 and published PCT Application Nos. WO 00/10456 and WO 01/67035, the entire contents of each of which are incorporated herein by reference. Other configurations are also contemplated including a 5 DOF and 3 DOF system without departing from the scope of the present disclosure. Tracking system 70 is configured for use with catheter guide assemblies 90 to track the position of the EM sensor 94 as it moves in conjunction with the EWC 96 through the airways of the patient.

As shown in FIG. 1, electromagnetic field generator 76 is positioned beneath the patient. Electromagnetic field generator 76 and the plurality of reference sensors 74 are interconnected with tracking module 72, which derives the location of each reference sensor 74 in six DOF. One or more of reference sensors 74 are attached to the chest of the patient. The six DOF coordinates of reference sensors 74 are sent to workstation 80, which includes application 82 where sensors 74 are used to calculate a patient coordinate frame of reference. In practice, a clinician uses the catheter guide assembly 90 to navigate the EWC 96 and/or bronchoscope 50 using the EM sensor 94 to reach a target site from within the luminal network of the lungs (e.g., the airways). Once the target site is reached, another device, e.g., a medical tool, is inserted into the EWC 96 and/or bronchoscope 50 and advanced to the target site.

Figure 2:
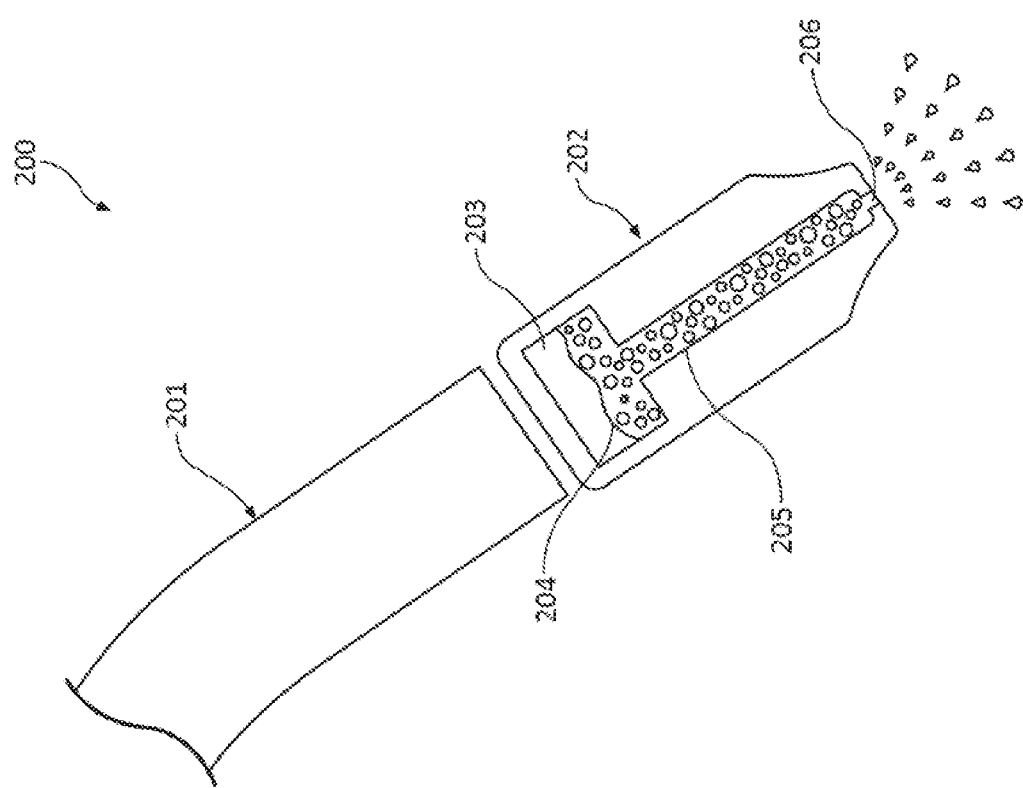
FIG. 2 is a partial perspective view showing the distal portion of a medical tool configured for use with the system of FIG. 1.

With reference to FIG. 2, the distal portion of a medical tool for use with the present disclosure is illustrated and generally identified by reference numeral 200. Medical tool 200 includes a flexible elongate member 201, a body 202, a reservoir 203 filled with a therapeutic and diagnostic agent 204, a lumen 205, and a nozzle 206. Medical tool 200 may be, e.g., a small atomizer or aerosolizer, which may be similar in design to an inhaler or nebulizer. Medical tool 200 may also be a liquid, gel, or gas dispensing device configured to dispense therapeutic and/or diagnostic agents. For example, in addition to dispensing therapeutic agents used to treat tissue, medical tool 200 may additionally or alternatively dispense diagnostic agents, e.g., radio-labeled ligands to identify an infection in a certain lung region or a marker that auto fluoresces when in contact with certain forms of lung injury just to name a few.

Flexible elongate member 201 is configured to be extendable within bronchoscope 50 or EWC 96. Body 202 of medical tool 200 may be attached to a distal end portion of flexible elongate member 201. A therapeutic agent 204 may be any of a variety of medication, including but not limited bronchidilators, corticosteroids, methylxanthines, beta-agonists, inhibitors, antimicrobials, antitumor agents, antifibrotic agents, biologic agents, immunotherapy, gene vectors, and radio-labeled and auto fluorescing ligands. A diagnostic agent 204 may be inorganic and organic compounds, dyes, stains, radioactive tracers, and culture-media chemical based constituents. Other suitable therapeutic and diagnostic agents known in the art are also contemplated and are configured for use with the medical tool 200 described herein. In embodiments, medical tool 200 is configured to dispense a therapeutic agent 204 and a diagnostic agent 204 together, or independently, as desired. In one example, the particles of the therapeutic and diagnostic agent 204 may utilize time release technology for timed or continuous drug delivery of the medication or drugs contained therein over an extended period time. In another embodiment, therapeutic and diagnostic agent 204 may be micro-particles. The micro-particles may be small enough such that they are not lodged within the luminal network of the lungs before reaching their target destination, but also large enough to traverse the alveoli of the lungs. For example, the micro-particles may be from 5-15 microns, although any suitable particle size is contemplated. In embodiments, if a sensor 94 is incorporated into or onto the bronchoscope 50, the working channel of the bronchoscope 50 itself can then become the source of localized delivery for a diagnostic and/or therapeutic substance.

In use, medical tool 200 is inserted into EWC 96 and/or bronchoscope 50 and navigated through the lungs until nozzle 206 is proximate to the target site identified during the planning phase. Once nozzle 206 of medical tool 200 is proximate to the target site, medical tool 200 is actuated, upon which therapeutic and diagnostic agent 204 is released as, e.g., micro-particles, liquid, or the like, as shown in FIG. 2. It should be appreciated that medical tool 200 may employ a variety of technologies for accomplishing the release and dispersal of the therapeutic and diagnostic agent 204. This may include one or more lumens extending to the proximal end of the flexible elongate member 201 for the injection of a medium for atomizing or aerosolizing therapeutic and diagnostic agent 204 (e.g., a propellant source). Alternatively, a mechanism may be incorporated to selectively release therapeutic and diagnostic agent 204 from reservoir 203, where the reservoir 203 itself is pressurized. In such an embodiment, the reservoir 203 may be removable from medical tool 200. Actuation of the selectively releasable mechanism may be accomplished from the proximal end of the medical tool 200 and may be mechanical, electrical, or a combination of the two.

The therapeutic and diagnostic agent 204 may be in the form of a gel or paste for highly localized treatment of an identified location, particularly where it is desirable that the therapeutic and diagnostic agent 204 not be widely dispersed or where longer-term adherence to the treatment area is desired. As will be understood by those of skill in the art, further mechanisms for localized application of therapeutic and diagnostic agent 204 may be employed without departing from the scope of the present disclosure.

Figure 3:
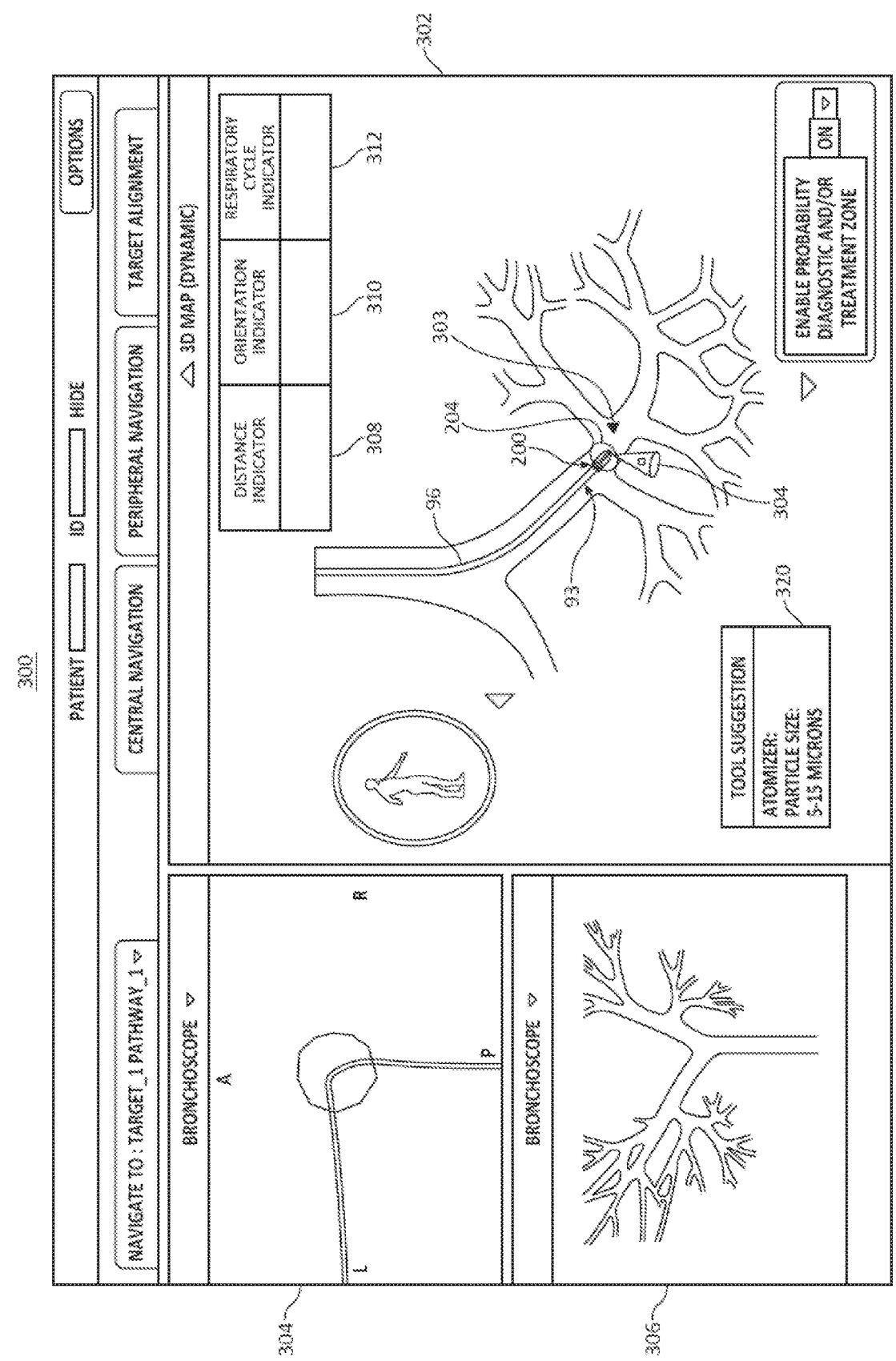
FIG. 3 is an illustration of a user interface of the workstation of FIG. 1 presenting multiple views for navigating to a target site.

FIG. 3 depicts a user interface that may be presented on display 81 (FIG. 1) during a patient assessment and/or procedure to locally treat the airways of a patient. As shown in FIG. 3, in accordance with embodiments of the present disclosure, display 81 presents user interface 300 to the clinician with a number of views 302, 304, and 306, to assist the clinician in navigating locatable guide 92 and EWC 96 to assess and treat e.g., a target site 303. User interface 300 may include a local view (3D map static) 302, a bronchoscope view 304, and a 3D map dynamic view 306. Local view 302 may also present the clinician with a visualization of distal tip 93 of EWC 96, EM sensor 94 of locatable guide 92, and medical tool 200 as appropriate during navigation. Bronchoscope view 304 may present an actual real-time view of the patient's lungs, e.g., by using a camera (not shown) and a light source (not shown). Bronchoscope view 304 may be used in conjunction with views 302, 306 to navigate the luminal network of the lungs. Additionally or alternatively, bronchoscope view 304 may be used to assess, in real time, the efficacy of a drug at the intended target site. For example, changes in the lungs and lung lobes, airway and blood vessel volume, or the like, may be measured, following application of therapeutic and diagnostic agent 204 (FIG. 2), using bronchoscope view 304. Other views may be presented without departing from the scope of the present disclosure. As EWC 96 and locatable guide 92 advance, each of the views 302, 304, and 306 is updated to account for the change in location.

User interface 300 may additionally include distance indicator 308, orientation indicator 310, and respiratory cycle indicator 312 which provide feedback on distance to target site 303, orientation with respect to target site 303, and sufficient access to target site 303 during the respiratory cycle. In one embodiment, indicators 308, 310, 312 may alternate between two colors or two shapes depending on the distance and orientation. For example, and as stated herein, when the distance to target site 303 from distal tip 93 of EWC 96 is within the distance of interaction for medical tool 200, distance indicator 308 may change color from red to green or change from an "X" to a check mark as an indicator that from the current location to target site 303, medical tool 200 is capable of interacting. In addition, orientation indicator 310 may change based on the orientation of medical tool 200 with respect to target site 303 and the adequacy of medical tool 200 interacting with target site 303. Respiratory cycle indicator 312 may provide audio feedback to the clinician indicating where in the respiratory cycle the patient is at any one time and during when a peak of respiration interaction with region of interest 303 is likely to occur.

In further embodiments, user interface 300 may include a tool suggestion window 320. During the respiratory cycle, tracking system 70 may analyze the movement of the airways during both inhalation and exhalation and based on the movement of the airway and the movement of target site 303. User interface 300 may provide with suggestion interface window 320, a specific medical tool 200 (including a specific therapeutic agent) or other tools, which are useful based on movement during the respiratory cycle, the specific assessment and/or procedure, and other characteristics that may be affected by the respiratory cycle. In further embodiments, user interface 300 may also provide a display of a confidence rating of interacting with target site 303, detailing the percentage likelihood of interacting with target site 303.

In use, the functional respiratory map of user interface 300 may be used to navigate, assess, and treat a target site. Initially, during the planning phase, the 3D map static view 302 and/or 3D map dynamic view 306 are used to make an assessment of a condition. For example, as described above, a user may perform a VQ scan and utilize user interface 300 to make a real time assessment as to where inhaled particles ultimately disperse to in the lungs (e.g., the deposition pattern) and where the most functional lung and gas exchange occurs. Using this and/or other methods, a clinician may then determine where to concentrate treatment, what treatment to use, and how much treatment to use, e.g., on target site 303. Once the target site 303 is identified, using the planned procedure, a clinician may insert medical tool 200 into EWC 96 and/or bronchoscope 50 and advance it to target site 303 following a pathway depicted in the bronchoscope view 304 and the dynamic 3D map view 302 follow the plan to arrive at a target site 303. When medical tool 200 is proximate to target site 303, a clinician may activate medical tool 200 such that therapeutic and diagnostic agent 204 is dispensed from nozzle 206 to treat target site 303 directly.

It should be appreciated that delivering a medication directly to target site 303 will enable a clinician to, e.g., better treat target site 303, better assess the true efficacy of a particular medication, and to save medication. Moreover, delivering, e.g., therapeutic and diagnostic agent 204 directly to target site 303 utilizing user interface 300 allows a clinician to assess, in real-time, the efficacy of any particular medication. After treatment, a clinician may perform another CT scan to generate a post-treatment 3D model of the patient's lungs, which can then be compared with the pre-treatment data of the patient's lungs to assess the efficacy of the treatment. Specifically, utilizing user interface 300, a clinician can measure the therapeutic responses to the treatment, e.g., the measured changes from pre and post-treatment data, such as, for example, changes in the lungs and lung lobes, airway and blood vessel volume, measures of flow both with respect to the entire system as well as specific areas of the system, for example, the right upper lobe, the left upper lobe, etc.

In an alternative embodiment, a therapeutic and diagnostic agent 204 may be administered in a simplified outpatient assessment and/or procedure. A clinician may insert bronchoscope 50 (e.g., a pediatric bronchoscope) and/or EWC 96 down a patient's mouth or nose. A clinician may then manipulate bronchoscope 50 and/or EWC 96 until the desired target site in the lungs is reached. A camera (not shown) or light source (not shown) may be used to navigate the lungs to the intended target site. Medical tool 200 may then be advanced down bronchoscope 50 and/or EWC 96 until nozzle 206 is proximate to the target site, upon which medical tool may be activated to dispense therapeutic and diagnostic agent 204 onto the intended target site. The bronchoscope 50 and/or EWC 96 may then be navigated to a target site in the airways or lung parenchyma. This assessment and/or procedure may be automated relative to the sequence of airways or targets that need to be treated and in addition, to the type of therapeutic and diagnostic agents assigned to a particular target. The treatment may be based initially on pre-treatment assessment of the parenchyma and airway tree as well as by using a data base to further enhance selection and accuracy. In addition, follow up treatments may then also be based on how a patient responded to the previous treatment, which data can then be integrated into the next treatment plan. The data can be used to develop a database to optimize patient treatment over time relative to the disease or affliction being targeted.

Thus, the presently described embodiment ensures delivery of therapeutic and diagnostic agent 204 to the target site in an efficient, simplified outpatient assessment and/or procedure.

Detailed embodiments of devices, systems incorporating such devices, and methods using the same have been described herein. However, these detailed embodiments are merely examples of the disclosure, which may be embodied in various forms. Therefore, specific structural and functional details disclosed herein are not to be interpreted as limiting, but merely as a basis for the claims and as a representative basis for allowing one skilled in the art to employ the present disclosure in virtually any appropriately detailed structure. While the preceding embodiments were described in terms of bronchoscopy of a patient's airways, those skilled in the art will realize that the same or similar devices, systems, and methods may be used in other luminal networks, such as, for example, the vascular, lymphatic, and/or gastrointestinal networks as well.

What is claimed is:

1. A system, comprising:
   a display presenting one or images of a patient's lungs;
   a user interface presented on the display configured to present a 3D model of a luminal network, wherein the 3D model is configured to assist a clinician in navigating to a target site within the luminal network;
   a working channel navigable within the luminal network; and
   a medical tool including:
     a flexible elongate member having a distal end; and
     a therapeutic and diagnostic agent dispenser disposed at the distal end of the flexible elongate member, the therapeutic and diagnostic agent dispenser defining:
       a reservoir configured to store at least one of a therapeutic or diagnostic agent;
       a lumen in fluid communication with the reservoir; and
       a nozzle disposed at a distal end of the lumen, wherein the therapeutic and diagnostic agent dispenser is configured to dispense aerosolized particles from the reservoir through the lumen, and from the lumen through the nozzle to treat the target site, the flexible elongate member and the therapeutic and diagnostic agent dispenser configured for advancement through the working channel to deliver the aerosolized particles directly to the target site for absorption within the target site.

2. The system of claim 1, wherein the aerosolized particles are selected from the group consisting of liquids, gases, and gels.

3. The system of claim 2, wherein each particle of the aerosolized particles is between 5 and 15 microns in diameter upon dispensation.

4. The system of claim 2, wherein the user interface is configured to assess an efficacy of the aerosolized particles.

5. The system of claim 2, wherein the user interface is configured to compare a pre-treatment 3D model of the luminal network with a post-treatment 3D model of the luminal network such that an efficacy of the aerosolized particles can be determined.

6. The system of claim 1, wherein the therapeutic and diagnostic agent dispenser is an aerosol emitting device for deploying the aerosolized particles onto the target site.

7. The system of claim 1, wherein the therapeutic and diagnostic agent dispenser is an atomizer.

8. The system of claim 1, wherein the therapeutic and diagnostic agent dispenser is a nebulizer.

9. The system of claim 1, wherein the 3D model of the luminal network is formed from a computed tomography (CT) scan, the 3D model configured to be merged together with images from a second imaging modality to facilitate navigation through the lung's airways and to treat tissue.

10. The system of claim 1, wherein a therapeutic agent is selected from the group consisting of bronchidilators, corticosteroids, methylxanthines, beta-agonists, inhibitors, antimicrobials, antitumor agents, antifibrotic agents, biologic agents, immunotherapy, gene vectors, radio-labeled and auto fluorescing ligands.

11. The system of claim 1, wherein a diagnostic agent is selected from the group consisting of inorganic and organic compounds, dyes, stains, radioactive tracers, and culture-media chemical based constituents.

12. The system of claim 1, wherein the therapeutic and diagnostic agent dispenser is removably coupled to the distal end of the flexible elongate member.

13. A medical tool, comprising:
a flexible elongate member configured to navigate through a luminal network to a target site via a guide catheter; and
a diagnostic agent dispenser disposed at a distal end of the flexible elongate member, the diagnostic agent dispenser including:
a reservoir configured to store a diagnostic agent, the diagnostic agent selected from the group consisting of inorganic and organic compounds, dyes, stains, radioactive tracers, and culture-media chemical based constituents;
a lumen in fluid communication with the reservoir; and
a nozzle disposed at a distal end of the lumen, wherein the diagnostic agent is configured to dispense aerosolized particles of the diagnostic agent from the reservoir through the lumen and out of the nozzle for diagnosing the target site.

14. The medical tool of claim 13, wherein the diagnostic agent dispenser is removably coupled to the distal end of the flexible elongate member.

15. The medical tool of claim 13, wherein the aerosolized particles are selected from the group consisting of liquids, gases, and gels.

16. The medical tool of claim 13, wherein the diagnostic agent dispenser is configured to store a therapeutic agent, the therapeutic agent being selected from the group consisting of bronchidilators, corticosteroids, methylxanthines, beta-agonists, inhibitors, antimicrobials, antitumor agents, antifibrotic agents, biologic agents, immunotherapy, gene vectors, radio-labeled and auto fluorescing ligands.

17. The medical tool of claim 13, wherein each particle of the aerosolized particles is between 5 and 15 microns in diameter upon dispensation.

18. A medical tool, comprising:
a flexible elongate member configured to navigate through a luminal network to a target site via a guide catheter; and
a therapeutic agent dispenser removably coupled to a distal end of the flexible elongate member, the therapeutic agent dispenser including:
a reservoir configured to store a therapeutic agent therein, the therapeutic agent selected from the group consisting of bronchidilators, corticosteroids, methylxanthines, beta-agonists, inhibitors, antimicrobials, antitumor agents, antifibrotic agents, biologic agents, immunotherapy, gene vectors, radio-labeled and auto fluorescing ligands;
a lumen in fluid communication with the reservoir; and
a nozzle disposed at a distal end of the lumen, wherein the therapeutic agent dispenser is configured to dispense aerosolized particles of the therapeutic agent from the reservoir through the lumen to treat the target site.

19. The medical tool of claim 18, wherein the aerosolized particles are selected from the group consisting of liquids, gases, and gels.

20. The medical tool of claim 18, wherein each particle of the aerosolized particles is between 5 and 15 microns in diameter upon dispensation.

21. The medical tool of claim 18, wherein the therapeutic agent dispenser is configured to store and dispense a diagnostic agent.

* * * * *